United States Patent
Sanford et al.

(10) Patent No.: US 10,913,696 B2
(45) Date of Patent: Feb. 9, 2021

(54) METHOD FOR AROMATIC FLUORINATION

(71) Applicants: DOW GLOBAL TECHNOLOGIES LLC, Midland, MI (US); The REGENTS OF THE UNIVERSITY OF MICHIGAN, Ann Arbor, MI (US)

(72) Inventors: Melanie S. Sanford, Ann Arbor, MI (US); Douglas Bland, Midland, MI (US); Patrick S. Hanley, Midland, MI (US); Megan A. Cismesia, Midland, MI (US); Sydonie D. Schimler, Ann Arbor, MI (US)

(73) Assignees: Dow Global Technologies LLC, Midland, MI (US); The Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 16/847,193

(22) Filed: Apr. 13, 2020

(65) Prior Publication Data
US 2020/0239390 A1 Jul. 30, 2020

Related U.S. Application Data

(62) Division of application No. 16/098,296, filed as application No. PCT/US2017/030608 on May 2, 2017, now Pat. No. 10,654,776.

(60) Provisional application No. 62/408,270, filed on Oct. 14, 2016, provisional application No. 62/376,967, filed on Aug. 19, 2016, provisional application No. 62/362,721, filed on Jul. 15, 2016, provisional application No. 62/330,311, filed on May 2, 2016.

(51) Int. Cl.
| | |
|---|---|
| C07C 17/02 | (2006.01) |
| C07D 453/02 | (2006.01) |
| C07D 311/16 | (2006.01) |
| C07C 17/093 | (2006.01) |
| C07D 209/08 | (2006.01) |
| C07D 213/79 | (2006.01) |
| C07D 213/61 | (2006.01) |
| C07C 231/12 | (2006.01) |
| C07C 41/22 | (2006.01) |
| C07C 45/63 | (2006.01) |
| C07D 213/57 | (2006.01) |
| C07C 201/12 | (2006.01) |
| C07C 67/307 | (2006.01) |
| C07D 213/75 | (2006.01) |
| C07J 21/00 | (2006.01) |
| C07D 279/16 | (2006.01) |
| C07C 253/30 | (2006.01) |
| C07D 209/88 | (2006.01) |
| C07D 215/18 | (2006.01) |
| C07C 25/13 | (2006.01) |
| C07C 317/14 | (2006.01) |

(52) U.S. Cl.
CPC ............ *C07C 17/02* (2013.01); *C07C 17/093* (2013.01); *C07C 25/13* (2013.01); *C07C 41/22* (2013.01); *C07C 45/63* (2013.01); *C07C 67/307* (2013.01); *C07C 201/12* (2013.01); *C07C 231/12* (2013.01); *C07C 253/30* (2013.01); *C07C 317/14* (2013.01); *C07D 209/08* (2013.01); *C07D 209/88* (2013.01); *C07D 213/57* (2013.01); *C07D 213/61* (2013.01); *C07D 213/75* (2013.01); *C07D 213/79* (2013.01); *C07D 215/18* (2013.01); *C07D 279/16* (2013.01); *C07D 311/16* (2013.01); *C07D 453/02* (2013.01); *C07J 21/008* (2013.01)

(58) Field of Classification Search
CPC .................................................... C07C 17/02
See application file for complete search history.

(56) References Cited

U.S. PATENT DOCUMENTS

| | | | |
|---|---|---|---|
| 9,878,983 B2 * | 1/2018 | Sanford | C07D 215/18 |
| 10,654,776 B2 * | 5/2020 | Sanford | C07J 21/008 |

FOREIGN PATENT DOCUMENTS

WO 2012/142162 10/2012

OTHER PUBLICATIONS

Fujimoto, Teppei et al. "PhenoFluorMix: Practical Chemoselective Deoxyfluorination of Phenols" Organic Letters (2015) vol. 17, pp. 544-547.

(Continued)

*Primary Examiner* — Golam M Shameem
(74) *Attorney, Agent, or Firm* — McDonnell Boehnen Hulbert & Berghoff LLP

(57) ABSTRACT

Disclosed is a fluorination method comprising providing an aryl fluorosulfonate and a fluorinating reagent to a reaction mixture; and reacting the aryl fluorosulfonate and the fluorinating reagent to provide a fluorinated aryl species.

Also disclosed is a fluorination method comprising providing, a salt comprising a cation and an aryloxylate, and $SO_2F_2$ to a reaction mixture; reacting the $SO_2F_2$ and the ammonium salt to provide a fluorinated aryl species.

Further disclosed a fluorination method comprising providing a compound having the structure Ar—OH to a reaction mixture; where Ar is an aryl or heteroaryl; providing $SO_2F_2$ to the reaction mixture; providing a fluorinating reagent to the reaction mixture; reacting the $SO_2F_2$, the fluorinating reagent and the compound having the structure Ar—OH to provide a fluorinated aryl species having the structure Ar—F.

20 Claims, No Drawings

(56) References Cited

OTHER PUBLICATIONS

Schimler, Sydonie D. et al. "Nucleophilic Deoxyfluorination of Phenols via Aryl Fluorosulfonate Intermediates" Journal of the American Chemical Society (2017) vol. 139, pp. 1452-1455.
The International Search Report (ISR) with Written Opinion for PCT/US2017/030608 dated Jun. 22, 2017, pp. 1-13.

* cited by examiner

METHOD FOR AROMATIC FLUORINATION

CROSS-REFERENCE TO RELATED APPLICATIONS

This application is a divisional application of U.S. application Ser. No. 16/098,296, filed Nov. 1, 2018, which is a U.S. national phase of International Application No. PCT/US2017/030608, filed May 2, 2017, which claims the benefit of priority to U.S. Provisional Application No. 62/408,270, filed, Oct. 14, 2016, and to U.S. Provisional Application No. 62/376,967, filed Aug. 19, 2016, and to U.S. Provisional Application No. 62/362,721, filed Jul. 15, 2016, and to U.S. Provisional Application No. 62/330,311, filed May 2, 2016, the disclosures of which are incorporated herein by reference in their entirety.

BACKGROUND

Selectively fluorinated aromatic compounds having a carbon-fluorine (C—F) bond are often biologically active and can be used as active components of many drugs and agrochemicals. A common strategy for the formation of these C—F bonds is through nucleophilic aromatic substitution by replacing an aryl-X bond, where X is, for example, Cl, Br, or NO2. Recent methodologies have demonstrated that phenols and their derivatives—where X is, for example, OH or trifluoromethanesulfonate—can be used, although expensive reagents are required.

An improved method for fluorinating aromatic compounds is desired.

SUMMARY

In a broad aspect, this disclosure provides a method for preparing aryl fluorides, the method comprising forming a reaction mixture comprising an aryl fluorosulfonate and a fluorinating reagent, optionally in a solvent system. The reaction is permitted to proceed for a period of time, after which the desired product may be isolated.

In another broad aspect, this disclosure provides a method for preparing aryl fluorides, the method comprising forming a reaction mixture comprising an aryloxylate salt and sulfuryl fluoride, optionally in a solvent system. The resulting reaction mixture is permitted to react for a period of time, after which the desired product may be isolated.

In yet another broad aspect, this disclosure provides a method for preparing aryl fluorides, the method comprising forming a reaction mixture comprising an aryl hydroxy compound of formula Ar—OH, wherein Ar represents an aryl or heteroaryl group, sulfuryl fluoride, and a fluorinating reagent, optionally in a solvent system. The resulting reaction mixture is permitted to react for a period of time, after which the desired product may be isolated.

According to a first embodiment, the present disclosure describes a fluorination method comprising providing a solvent to a reaction mixture or reaction vessel; providing an aryl fluorosulfonate to the reaction mixture or vessel; providing a fluorinating reagent to the reaction mixture or vessel; and reacting the aryl fluorosulfonate and the fluorinating reagent to provide a fluorinated aryl species.

According to a second embodiment, the present disclosure describes a fluorination method comprising providing a solvent to a reaction mixture or vessel; providing a salt comprising a cation and an aryloxylate to a reaction mixture or vessel; providing $SO_2F_2$ to the reaction mixture or vessel; and reacting the $SO_2F_2$ and the ammonium salt to provide a fluorinated aryl species.

According to a third embodiment, the present disclosure describes a fluorination method comprising providing a solvent to a reaction mixture or reaction vessel; providing a compound having the structure Ar—OH to a reaction mixture or vessel; where Ar is an aryl or heteroaryl group; providing $SO_2F_2$ to the reaction mixture or vessel; providing a fluorinating reagent to the reaction mixture or vessel; and reacting the $SO_2F_2$, the fluorinating reagent and the compound having the structure Ar—OH to provide a fluorinated aryl species having the structure Ar—F.

DETAILED DESCRIPTION

"Alkyl," as used in this specification, whether alone or as part of another group (e.g., in dialkylamino), encompasses straight, cyclic and branched chain aliphatic groups having the indicated number of carbon atoms. If no number is indicated (e.g., aryl-alkyl-), then 1-12 alkyl carbons are contemplated. Preferred alkyl groups include, without limitation, methyl, ethyl, propyl, isopropyl, butyl, isobutyl, sec-butyl, tert-butyl, pentyl, hexyl and tert-octyl.

The term "heteroalkyl" refers to an alkyl group as defined above with one or more heteroatoms (nitrogen, oxygen, sulfur, phosphorus) replacing one or more carbon atoms within the radical, for example, an ether or a thioether.

An "aryl" group refers to any functional group or substituent derived from an aromatic ring. In one instance, aryl refers to an aromatic moiety comprising one or more aromatic rings. In one instance, the aryl group is a $C_6$-$C_{18}$ aryl group. In one instance, the aryl group is a $C_6$-$C_{10}$ aryl group. In one instance, the aryl group is a $C_{10}$-$C_{18}$ aryl group. Aryl groups contain 4n+2 pi electrons, where n is an integer. The aryl ring may be fused or otherwise attached to one or more heteroaryl rings, aromatic or non-aromatic hydrocarbon rings or heterocycloalkyl rings. Preferred aryls include, without limitation, phenyl, naphthyl, anthracenyl, and fluorenyl. Unless otherwise indicated, the aryl group is optionally substituted with 1 or more substituents that are compatible with the syntheses described herein. Such substituents include, but are not limited to, sulfonate groups, boron-containing groups, alkyl groups, nitro groups, halogens, cyano groups, carboxylic acids, esters, amides, $C_2$-$C_8$ alkene, and other aromatic groups. Other substituents are known in the art.

"Heteroaryl" refers to any functional group or substituent derived from an aromatic ring and containing at least one heteroatom selected from nitrogen, oxygen, and sulfur. Preferably, the heteroaryl group is a five or six-membered ring. The heteroaryl ring may be fused or otherwise attached to one or more heteroaryl rings, aromatic or non-aromatic hydrocarbon rings or heterocycloalkyl rings. Examples of heteroaryl groups include, without limitation, pyridinyl, pyrimidinyl, pyridazinyl, pyrrolyl, triazinyl, imidazolyl, triazolyl, furanyl, thienyl, oxazolyl, and thiazolyl. The heteroaryl group may be optionally substituted with one or more substituents that are compatible with the syntheses described herein. Such substituents include, but are not limited to, fluorosulfonate groups, boron-containing groups, $C_1$-$C_8$ alkyl groups, nitro groups, halogens, cyano groups, carboxylic acids, esters, amides, $C_2$-$C_8$ alkene and other aromatic groups. Other substituents are known in the art.

"Carboxylic esters" refers to any functional group or substituent having a carboxylic acid ester component and may include straight chain, branched, or cyclo alkyl, aromatic, or perfluoroalkyl substituents.

"Alkoxy" refers to any functional group or substituent have an ether component and may include straight chain, branched, or cyclo alkyl, aromatic, heteroaromatic, or perfluoroalkyl substituents.

The present disclosure describes an improved method of fluorinating aromatic compounds described by the reaction Scheme I below:

(Scheme I)

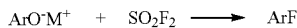

The product of the reaction in Scheme I is a fluorinated aryl compound, ArF.

In the embodiment depicted by Scheme I, sulfuryl fluoride —$SO_2F_2$— is provided to a reaction vessel which optionally contains solvent. The sulfuryl fluoride, which is a gas commercially available as a fumigant, can be bubbled into the solvent.

As shown in Scheme I, a salt is provided to the reaction vessel. Although the order of addition is irrelevant, the salt is typically added after the sulfuryl fluoride to form a reaction mixture. The salt comprises a cation—identified as M—and a aryloxylate, preferably phenolate,—identified as ArO. It is understood that the phenolate may be added to the reaction mixture in the hydroxyl form or the ionic form and that the solution will reach an equilibrium between the two forms. The group Ar is an aryl or heteroaryl group, and is alternatively further substituted. Suitable substituents for further substituting the phenolate include alkyl, heteroalkyl, cyano, halides, carboxylic esters, perfluoroalkyl or alkoxy groups.

The sulfuryl fluoride is typically used in reactions according to Scheme I in a molar excess relative to the amount of aryloxylate. Suitable molar ratios of sulfuryl fluoride to aryloxylate are from about 1:1 to about 10:1, or 1:1 to 2:1, or 1:1 to 5:1, or 2:1 to 5:1, or 2:1 to 3:1.

The cation is selected such that it is suitable for forming a fluorinating reagent in situ. Examples of suitable cations include tetraalkylammoniums, sodium, potassium, cesium, or combinations thereof. Examples of tetraalkylammoniums include tetramethylammonium, tributylmethylammonium and tetrabutylammonium. In one instance, the tetraalkylammoniums include 4 alkyl substituents, each $C_1$-$C_4$.

In Scheme I, the reaction may be carried out in the presence of a solvent. Alternatively, when both the starting material and product are liquids at, for example, room temperature, the reaction may be carried out in the absence of a solvent, i.e., neat, to simplify isolation and purification of the product.

In reactions in which the solvent is employed, the solvent may be a polar aprotic solvent. Examples of suitable polar aprotic solvents include dimethyl formamide (DMF), dimethyl sulfoxide (DMSO), N-methyl-2-pyrrolidone, dimethylacetamide (DMA), 1,3-dimethyl-3,4,5,6-tetrahydro-2-pyrimidinone, dichloromethane (DCM), acetonitrile, ethyl acetate, hexamethylphosphoric triamide (HMPT), and 1,3-dimethyl-2-imidazolidinone. Alternatively the solvent may be an alkoxy ether solvent. Examples of suitable alkoxy ether solvents include tetrahydrofuran (THF), diglyme, and dimethoxyethane (DME). Other suitable solvents for the reaction are nitrile solvents. Benzonitrile is an example of a suitable nitrile solvent. Other solvents useful in the reaction are, aromatic solvents, such as for example, toluene.

The fluorination reactions depicted in Scheme I optionally carried out in the presence of a fluorinating reagent, MF, wherein M is as defined above. The fluorinating reagent may be used in an amount that is less than a molar equivalent of the amount of the aryloxylate.

The reaction depicted in Scheme I proceeds conveniently at temperatures of from about 0° C. to 200° C., or from room temperature, i.e., about 25° C. to about 100° C. Although reaction progress can be monitored via a variety of techniques, it is generally unnecessary to do so as the reactions described by Scheme I typically proceed to completion in about 12-36 hours, often within about 24 hours.

Without being limited by theory, it is believed that the reaction of the aryloxylate with sulfuryl fluoride as depicted in Scheme I proceeds as shown in the Scheme II below (where Ar and M are as defined above, and it is noted that it is not necessary that each M shown in this scheme be the same compound):

(Scheme II)

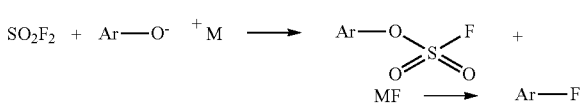

As can be seen, the sulfuryl fluoride reacts with the aryloxylate to form an aryl fluorosulfonate. The fluorosulfonate then becomes a leaving group allowing the fluorine to be joined to the aryl group at the location of the original oxygen atom.

Preferably, the reaction is performed in a substantially anhydrous environment. As the amount of water in the reaction increases, the product yield decreases.

In another embodiment, the reaction is performed using the aryl fluorosufonate as a starting material, as shown in reaction Scheme III (where A and M are as defined above):

(Scheme III)

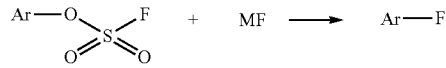

The aryl fluorosulfonate serving as the starting material in Scheme III can be prepared as described above. In one instance, the aryl fluorosulfonate can be prepared from the corresponding compound having a hydroxyl group in place of the —$OSO_2F$ group in a reaction mixture comprising $SO_2F_2$ and a base, as is known in the art. Reactions of the type depicted in Scheme III can be performed in the presence of solvent as defined above. In Scheme III, MF is a fluorinating reagent, wherein M is as defined above. Suitable fluorinating reagents include tetramethylammonium fluoride, sodium fluoride, potassium fluoride, cesium fluoride, lithium fluoride, tetrabutylammonium fluoride or combinations thereof. In certain embodiments, the reaction mixture further comprises a chloride group in addition to the fluorinating agent, for example, a combination of tetramethylammonium chloride and potassium fluoride. Typically, the fluorinating reagent, e.g., tetramethylammonium fluoride, is anhydrous when added to the reaction vessel.

The fluorination reactions depicted in Scheme III are carried out in the presence of a molar excess of fluorinating reagent, MF. Suitable molar ratios of fluorinating reagent MF to aryl fluorosulfonate are from about 1.1:1 to about 10:1, or 2:1 to 5:1, or 2:1 to 3:1.

The reactions depicted in Scheme III proceed conveniently at temperatures of from about 0° C. to 200° C., or from room temperature, i.e., about 25° C. to about 100° C. Although reaction progress can be monitored via a variety of techniques, it is generally unnecessary to do so as the reactions described by Scheme III typically proceed to completion in about 12-36 hours, often within about 24 hours.

In another embodiment, the reaction is performed using a starting material having the formula Ar—OH, where Ar is aryl or heteroaryl, to prepare a compound having the structure Ar—F. In this embodiment, the compound having the formula Ar—OH is provided to the reaction mixture in addition to a solvent, $SO_2F_2$, and a fluorinating reagent, as shown below in Scheme IV.

Scheme IV

Suitable fluorinating reagents MF include tetramethylammonium fluoride, sodium fluoride, potassium fluoride, cesium fluoride, tetrabutylammonium fluoride or combinations thereof. Alternatively, other MF, $SO_2F_2$ and Ar—OH can be combined with a different Lewis or Bronsted base to reduce the amount of fluorinating regent needed. In one instance, the reaction mixture further comprises a chloride salt or quaternary ammonium chloride compound in addition to the fluorinating agent, for example, a combination of tetramethylammonium chloride and potassium fluoride. The solvent, if present, is a polar aprotic solvent, as described herein.

The fluorination reactions depicted in Scheme IV are carried out in the presence of a molar excess of fluorinating reagent, MF. Suitable molar ratios of fluorinating reagent MF to Ar—OH are from about 1.1:1 to about 10:1, or about 2:1 to 5:1, or about 2:1 to 3:1, or about 3:1 to 4:1.

The sulfuryl fluoride is typically used in reactions according to Scheme IV in a molar excess relative to the amount of Ar—OH. Suitable molar ratios of sulfuryl fluoride to Ar—OH are from about 2:1 to about 10:1, or 2:1 to 5:1, or 2:1 to 3:1.

The reactions depicted in Scheme IV proceed conveniently at temperatures of from about 0° C. to 200° C., or from room temperature, i.e., about 25° C. to about 100° C. Although reaction progress can be monitored via a variety of techniques, is generally unnecessary to do so as the reactions described by Scheme IV typically proceed to completion in about 12-36 hours, often within about 24 hours.

In one instance, the reaction mixture does not contain a catalyst. One of the benefits of the reaction scheme described herein is that the scheme proceeds without the use of a catalyst.

The Examples that follow are illustrative of specific embodiments of the invention, and various uses thereof. They set forth for explanatory purposes only, and are not to be taken as limiting the invention.

Protection of certain reactive functionalities by introducing appropriate protecting groups may be necessary to achieve transformations within the scope of this disclosure. In general, the nature of and need for such protecting groups as well as the conditions necessary to attach and remove such groups will be apparent to those skilled in the art of organic synthesis. An authoritative account describing the many alternatives available to the trained practitioner can be found in "Protective Groups in Organic Synthesis", T. W. Greene and P. G. M. Wuts, Third edition, Wiley, N.Y. 1999. The protecting groups may be removed at a convenient subsequent stage using methods known from the art. Methods for removal of protecting groups are also described in the Greene and Wuts text.

EXAMPLES

Example 1

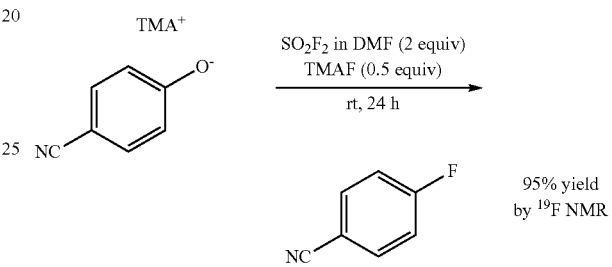

In a glovebox, tetramethylammonium 4-cyanophenolate (0.05 mmol, 1 equiv), tetramethylammonium fluoride (0.03 mmol, 0.5 equiv), and sulfuryl fluoride (0.14 M solution in DMF, 0.10 mmol, 2 equiv, prepared by bubbling sulfuryl fluoride gas through DMF) were added to a vial. The vial was sealed with a Teflon-lined cap and was allowed to stir for 24 hours at room temperature. After 24 h, the reaction mixture was diluted with dichloromethane and an internal standard (4-fluoroanisole) was added. The crude reaction mixture was analyzed by $^{19}F$ NMR spectroscopy.

Example 2

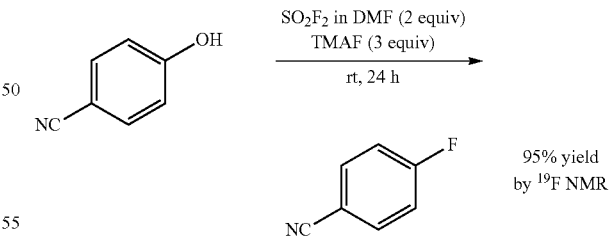

In a glovebox, 4-cyanophenol (0.05 mmol, 1 equiv), tetramethylammonium fluoride (0.15 mmol, 3 equiv), and sulfuryl fluoride (0.14 M solution in DMF, 0.10 mmol, 2 equiv, prepared by bubbling sulfuryl fluoride gas through DMF) were added to a vial. The vial was sealed with a Teflon-lined cap and was allowed to stir for 24 hours at room temperature. After 24 h, the reaction mixture was diluted with dichloromethane and an internal standard (4-fluoroanisole) was added. The crude reaction mixture was analyzed by $^{19}F$ NMR spectroscopy.

Example 3

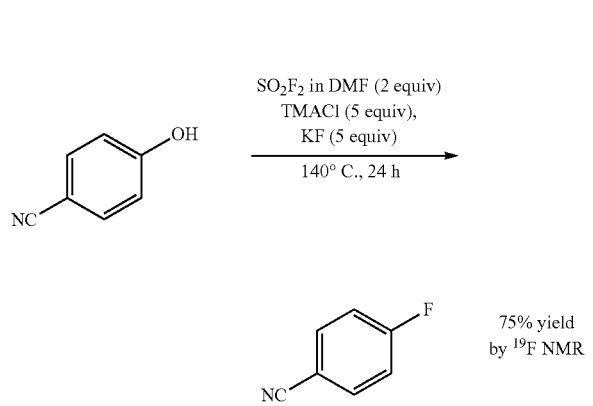

In a glovebox, 4-cyanophenol (0.05 mmol, 1 equiv), tetramethylammonium chloride (0.25 mmol, 5 equiv), potassium fluoride (0.25 mmol, 5 equiv), and sulfuryl fluoride (0.14 M solution in DMF, 0.10 mmol, 2 equiv, prepared by bubbling sulfuryl fluoride gas through DMF) were added to a vial. The vial was sealed with a Teflon-lined cap and was allowed to stir for 24 hours at 140° C. After 24 h, the reaction mixture was diluted with dichloromethane and an internal standard (4-fluoroanisole) was added. The crude reaction mixture was analyzed by $^{19}$F NMR spectroscopy.

Example 4

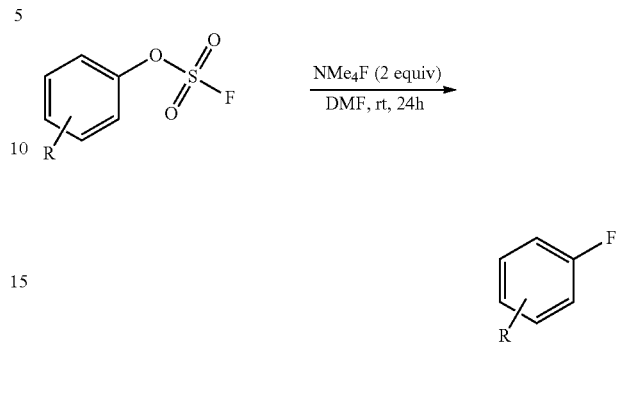

In a glovebox, a series of 4 mL vials (containing a stirbar) were each charged with one of the arylfluorosulfonate substrates identified in Table 1 (0.1 mmol, 1 equiv.) and anhydrous tetramethylammonium fluoride (18.6 mg, 0.2 mmol, number of equivalents listed in Table 1, referred to herein as "TMAF"). DMF (0.5 mL) was added, and each vial was sealed with a Teflon-lined cap. Each vial was removed from the glovebox and stirred at the temperature listed in Table 1 (where "RT" refers to room temperature). After 24 hours, each vial was diluted with dichloromethane (2 mL) and an internal standard (1,3,5-trifluorobenzene) was added. The crude reaction mixture was analyzed by 19F NMR spectroscopy and GCMS to confirm the Products and Yields listed in Table 1.

"Ph" in structures in Table 1 represents phenyl.

TABLE 1

| Arylfluorosulfonate substrate | Product | Temperature | TMAF equiv. | Yield |
|---|---|---|---|---|
| 4-NC-C6H4-OSO2F | 4-NC-C6H4-F | RT | 2 | 81% |
| 3-NC-C6H4-OSO2F | 3-NC-C6H4-F | RT | 2 | 80% |
| 2-NC-C6H4-OSO2F | 2-NC-C6H4-F | 80° C. | 2 | 51% |
| 4-EtO2C-C6H4-OSO2F | 4-EtO2C-C6H4-F | RT | 2 | 88% |

TABLE 1-continued
| Arylfluorosulfonate substrate | Product | Temperature | TMAF equiv. | Yield |
|---|---|---|---|---|
| 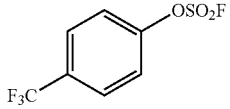 | 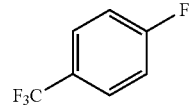 | RT | 2 | 67% |
|  | 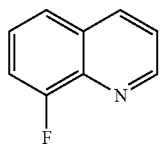 | 100° C. | 2 | 62% |
| 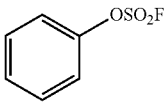 | 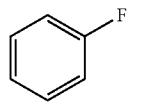 | 100° C. | 5 | 69% |
| 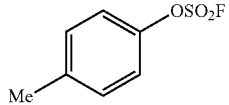 | 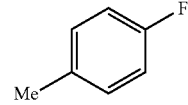 | 100° C. | 5 | 33% |
| 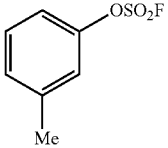 | 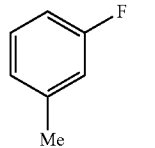 | 100° C. | 2 | 53% |
| 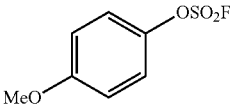 | 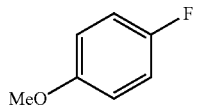 | 100° C. | 5 | 6% |
| 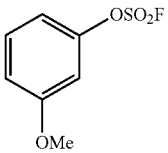 |  | 100° C. | 2 | 39% |
| 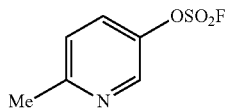 | 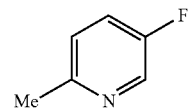 | 80° C. | 2 | 57% |
| 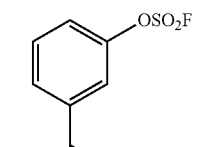 | 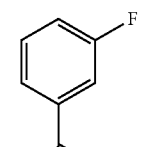 | 80° C. | 2 | 65% |
| 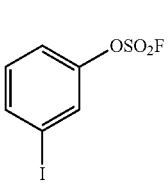 | 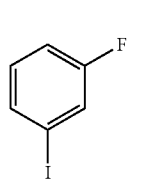 | 80° C. | 2 | 80% |

TABLE 1-continued

| Arylfluorosulfonate substrate | Product | Temperature | TMAF equiv. | Yield |
|---|---|---|---|---|
| 3-chlorophenyl fluorosulfonate | 1-chloro-3-fluorobenzene | 80° C. | 2 | 65% |
| 3-fluorophenyl fluorosulfonate | 1,3-difluorobenzene | 80° C. | 2 | 75% |
| 2-isopropyl-5-methylphenyl fluorosulfonate | 2-fluoro-1-isopropyl-4-methylbenzene | 100° C. | 5 | 27% |
| biphenyl-3-yl fluorosulfonate | 3-fluorobiphenyl | 100° C. | 2 | 69% |
| 4-(dimethylcarbamoyl)phenyl fluorosulfonate | 4-fluoro-N,N-dimethylbenzamide | 60° C. | 2 | 55% |
| 2-oxo-2H-chromen-7-yl fluorosulfonate | 7-fluoro-2H-chromen-2-one | 25° C. | 2 | 65% |
| 6-phenylpyridin-3-yl fluorosulfonate | 5-fluoro-2-phenylpyridine | 100° C. | 2 | 81% |
| 4-nitrophenyl fluorosulfonate | 1-fluoro-4-nitrobenzene | 80° C. | 2 | 55% |
| 4-chlorophenyl fluorosulfonate | 1-chloro-4-fluorobenzene | 25° C. | 2 | 75% |

TABLE 1-continued

| Arylfluorosulfonate substrate | Product | Temperature | TMAF equiv. | Yield |
|---|---|---|---|---|
| 2-phenylphenyl fluorosulfonate | 2-fluorobiphenyl | 100° C. | 2 | 95% |
| 1H-indol-4-yl fluorosulfonate | 4-fluoro-1H-indole | 25° C. | 2 | — |

Example 5

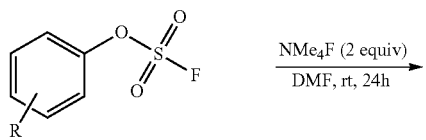

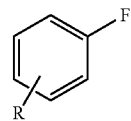

In a glovebox, a series of 4 mL vials (containing a stirbar) are each charged with one of the arylfluorosulfonate substrates identified in Table 2 (0.1 mmol, 1 equiv.) and anhydrous tetramethylammonium fluoride (18.6 mg, 0.2 mmol, 2 equiv). DMF (0.5 mL) is added, and each vial is sealed with a Teflon-lined cap. Each vial is removed from the glovebox and stirred at 80° C. for 24 hours. After 24 hours, each vial is diluted with dichloromethane (2 mL) and an internal standard (1,3,5-trifluorobenzene) is added.

TABLE 2

| Arylfluorosulfonate substrate | Product |
|---|---|
| naphthalen-1-yl fluorosulfonate | 1-fluoronaphthalene |
| naphthalen-2-yl fluorosulfonate | 2-fluoronaphthalene |
| 9-(fluorosulfonyl)-9H-carbazol-2-yl fluorosulfonate | 9-(fluorosulfonyl)-2-fluoro-9H-carbazole |
| isopropyl 5-(fluorosulfonyloxy)-6-phenylpicolinate | isopropyl 5-fluoro-6-phenylpicolinate |

Example 6

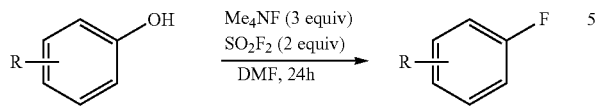

In a glovebox, a reactant as identified in Table 3 (1 equiv, 0.2 mmol) and TMAF (3 equiv, 0.6 mmol) were added to six 1 dram vial with stir bar. A 0.14 M solution of sulfuryl fluoride in DMF (2 equiv, 2.9 mL, 0.4 mmol) were added and each vial and were quickly sealed. Each vial was heated to the temperature indicated in Table 3 for 24 hours, and then cooled to room temperature before being diluted with ether. The organic layer of each reaction mixture was washed four times with water, dried over $MgSO_4$, filtered and concentrated. The crude material was purified by flash chromatography (20:1 pentane:ether). The yield of product for each reaction mixture is reported in Table 3.

Example 7

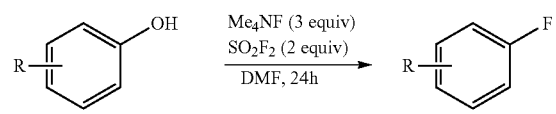

In a glovebox, a reactant as identified in Table 4 (1 equiv, 0.2 mmol) and TMAF (3 equiv, 0.6 mmol) are added to six 1 dram vial with stir bar (where "Me" is methyl and "Ac" is acetyl. A 0.14 M solution of sulfuryl fluoride in DMF (2 equiv, 2.9 mL, 0.4 mmol) are added and each vial and are quickly sealed. Each vial is heated to 80° C. for 24 hours, and then cooled to room temperature before being diluted with ether. The organic layer of each reaction mixture is washed four times with water, dried over $MgSO_4$, filtered and concentrated. The crude material is purified by flash chromatography (20:1 pentane:ether)

TABLE 3

| Vial | Reactant | Temperature | Yield | Product |
|------|----------|-------------|-------|---------|
| 1 | 4-cyanophenol | Room temperature | 56% | 4-fluorobenzonitrile |
| 2 | ethyl 4-hydroxybenzoate | Room temperature | 81% | ethyl 4-fluorobenzoate |
| 3 | 4-hydroxybenzophenone | Room temperature | 90% | 4-fluorobenzophenone |
| 4 | 4-phenylphenol | 100° C. | 85% | 4-fluorobiphenyl |
| 5 | 8-hydroxyquinoline | 100° C. | 53% | 8-fluoroquinoline |
| 6 | 4-phenoxyphenol | 100° C. | 68% | 4-fluorodiphenyl ether |

TABLE 4
| Reactant | Product |
|---|---|
| 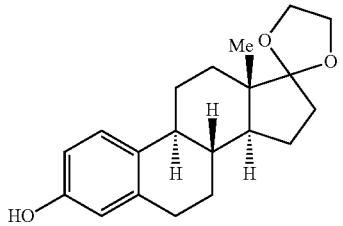 | 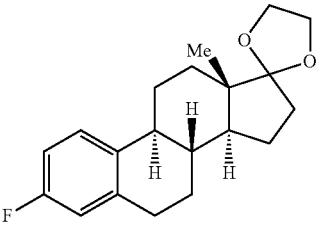 |
| 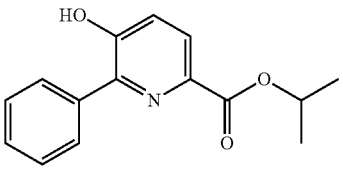 [SMILES: CC(C)OC(=O)c1ccc(O)c(-c2ccccc2)n1] | 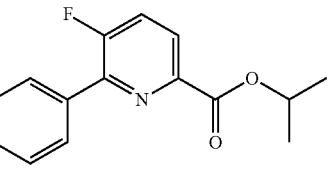 |
| 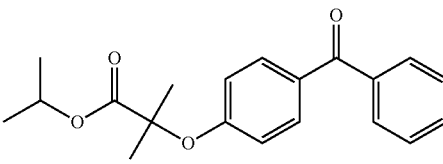 | 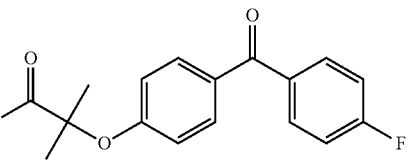 |
| 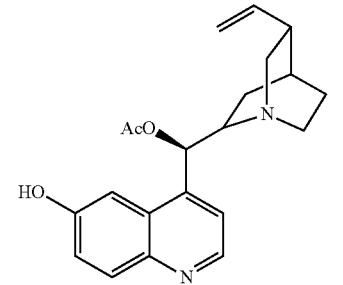 [SMILES: C=CC1CN2CCC1CC2[C@H](OC(C)=O)c1ccnc2ccc(O)cc12] | 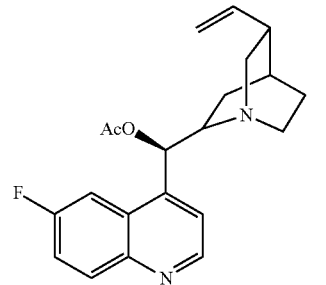 [SMILES: C=CC1CN2CCC1CC2[C@H](OC(C)=O)c1ccnc2ccc(F)cc12] |
| 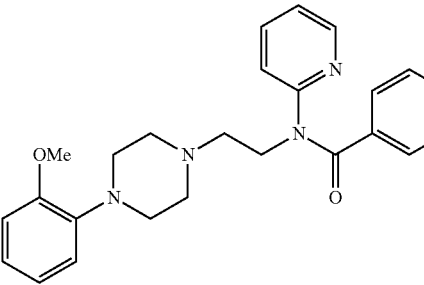 | 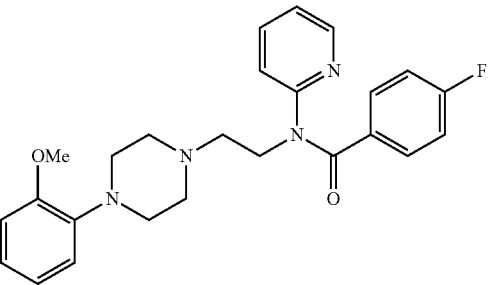 [SMILES: COc1ccccc1N1CCN(CCN(C(=O)c2ccc(F)cc2)c2ccccn2)CC1] |
| 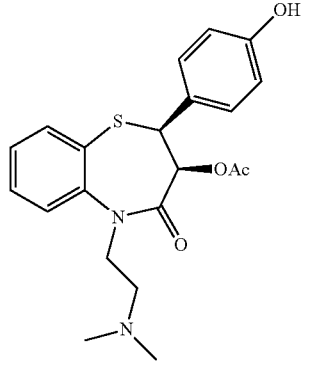 [SMILES: CC(=O)O[C@H]1C(=O)N(CCN(C)C)c2ccccc2S[C@H]1c1ccc(O)cc1] | 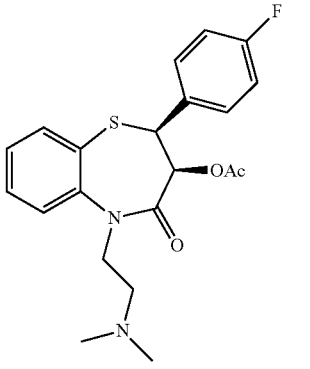 [SMILES: CC(=O)O[C@H]1C(=O)N(CCN(C)C)c2ccccc2S[C@H]1c1ccc(F)cc1] |

TABLE 4-continued

| Reactant | Product |
|---|---|
| 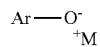 | |

What is claimed is:

1. A fluorination method comprising:
providing a salt having the following structure to a reaction mixture:

where Ar is an aryl or heteroaryl;
where M is a cation;
providing $SO_2F_2$ to the reaction mixture;
reacting the $SO_2F_2$ and the ammonium salt to provide a fluorinated aryl species having the following structure:

Ar—F.

2. A method according to claim 1, further comprising providing a solvent to the reaction mixture.

3. The fluorination method of claim 2, wherein the solvent is selected from the group consisting of polar aprotic solvents, alkoxy ether solvents, nitrile solvents, and aromatic solvents, or a mixture thereof.

4. The fluorination method of claim 1, wherein the cation is selected from the group consisting of, sodium, potassium, cesium, tetramethylammonium, and tetrabutylammonium.

5. The fluorination method of claim 3, wherein the cation is selected from the group consisting of, sodium, potassium, cesium, tetramethylammonium, and tetrabutylammonium.

6. A method according to claim 1, wherein

is tetramethylammonium 4-cyanophenolate.

7. A method according to claim 2, wherein the solvent comprises a polar aprotic solvent.

8. A method according to claim 2, wherein the solvent comprises an alkoxy ether solvent.

9. A method according to claim 2, wherein the solvent comprises a nitrile solvent.

10. A method according to claim 2, wherein the solvent comprises an aromatic solvent.

11. A method according to claim 3, wherein the cation is sodium.

12. A method according to claim 3, wherein the cation is potassium.

13. A method according to claim 3, wherein the cation is cesium.

14. A method according to claim 3, wherein the cation is tetramethylammonium.

15. A method according to claim 3, wherein the cation is tetrabutylammonium.

16. A method according to claim 2, wherein the solvent comprises dimethyl formamide, dimethyl sulfoxide, N-methyl-2-pyrrolidone, dimethylacetamide, 1,3-dimethyl-3,4,5,6-tetrahydro-2-pyrimidinone, dichloromethane, acetonitrile, ethyl acetate, hexamethylphosphoric triamide, or 1,3-dimethyl-2-imidazolidinone.

17. A method according to claim 2, wherein the solvent comprises DMF.

18. A method according to claim 2, wherein the solvent comprises tetrahydrofuran, diglyme, or dimethoxyethane.

19. A method according to claim 2, wherein the solvent comprises benzonitrile.

20. A method according to claim 2, wherein the solvent comprises toluene.

* * * * *